United States Patent [19]

Ohnmacht et al.

[11] 4,247,549
[45] Jan. 27, 1981

[54] PIPERAZINE-1-CARBOXYLIC ACID ESTERS POSSESSING ANTIDEPRESSANT OR ANALGESIC ACTIVITY

[75] Inventors: Cyrus J. Ohnmacht; Jeffrey B. Malick, both of Wilmington, Del.

[73] Assignee: ICI Americas Inc., Wilmington, Del.

[21] Appl. No.: 974,146

[22] Filed: Dec. 27, 1978

[51] Int. Cl.$^3$ .................. A61K 31/215; C07D 241/04
[52] U.S. Cl. ................................. 424/250; 424/14; 424/251; 424/263; 424/274; 424/304; 544/389; 544/390
[58] Field of Search .............. 544/389, 390; 424/250, 424/251

[56] References Cited

U.S. PATENT DOCUMENTS

| | | | |
|---|---|---|---|
| 2,535,971 | 12/1950 | Turner et al. | 544/389 |
| 2,617,803 | 11/1952 | Turner | 544/389 |
| 2,617,804 | 11/1952 | Goldman | 544/389 |
| 3,239,528 | 3/1966 | Bebenburg et al. | 544/390 |
| 3,401,224 | 9/1968 | Barrett et al. | 424/250 |

FOREIGN PATENT DOCUMENTS

| | | | |
|---|---|---|---|
| 273142 | 8/1969 | Austria | 544/389 |
| 2081564 | 12/1971 | France | 424/250 |

OTHER PUBLICATIONS

Lutz, et al., J. Org. Chem., 1947, vol. 12, pp. 771–775.
Chem. Abs., 1952, vol. 46, p. 8661.
I. Am. Chem. Soc., 1955, vol. 77, p. 4809–4811.
Chem. Abs., 1959, vol. 53, p. 8172.
Chem. Abs., 1959, vol. 53, p. 16168.
Chem. Abs., vol. 54, 1960, p. 9970.
Chem. Abs., vol. 54, 1960, pp. 12166 & 12169.
Chem. Abs., vol. 58, p. 3442, 1963.
J. Org. Chem., 1962, vol. 27, pp. 306–308.
Chem. Abs., 1963, vol. 58, p. 3442.
J. Med. Chem., 1963, vol. 6, pp. 541–544.
J. Med. Chem., 1964, vol. 7, pp. 241–242.
J. Pharm. Exptl. Therap., 1965, vol. 147, pp. 380–384, 391–398.
JACS, 1954, vol. 76, pp. 1164–1165.

*Primary Examiner*—Dale R. Ore
*Attorney, Agent, or Firm*—Cushman, Darby & Cushman

[57] ABSTRACT

Piperazine-1-carboxylic acid esters which are useful as antidepressants and as analgesics.

21 Claims, No Drawings

PIPERAZINE-1-CARBOXYLIC ACID ESTERS POSSESSING ANTIDEPRESSANT OR ANALGESIC ACTIVITY

The present invention is concerned with certain esters of piperazine-1-carboxylic acid which demonstrate useful antidepressant and analgesic activity.

According to one aspect of the invention a method is provided for obtaining antidepressant and analgesic effects in a warm-blooded host in need of such treatment by administering to the host an effective amount of a compound of formula (I):

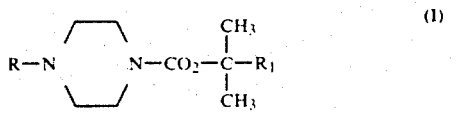

where R has a value as described hereinafter and $R_1$ is $CH_3$, $C\equiv CH$ or $CH=CH_2$. It is to be noted that the derivatives where $R_1$ is $CH_3$ or $C\equiv CH$ are generally preferred because of such factors as higher activity level or better chemical stability than the derivatives where $R_1$ is $CH=CH_2$. However, the latter are also considered generally suitable for use.

The compounds of formula (I) may be used in the form of pharmaceutically acceptable acid-addition salts. Suitable pharmaceutically acceptable salts include, for example, the hydrochlorides, hydrobromides, phosphates, sulphates, citrates, acetates, maleates and oxalates.

Piperazine derivatives having antidepressant and/or analgesic activity have previously been disclosed. For example, U.S. Pat. No. 3,401,224 describes the use of certain N-alkylpiperazines, especially N-benzylpiperazine, for the treatment of depression, colds or headaches. However, as far as can be ascertained, none of the piperazine derivatives previously disclosed as having antidepressant and/or analgesic activities has included the

group which characterizes the piperazine derivatives contemplated herein. This group appears to be responsible to an important degree for the unique combination of useful properties possessed by the formula (I) derivatives.

While the use of piperazine derivatives including the group (II) as antidepressants and/or analgesics appears to be broadly new, it is to be noted that certain of these derivatives which are suitable for use according to the invention, are known compounds. For example, Herrin et al (J. Med. Chem. 18, 1216, 1975) have described the following t-butyl esters for use as chemical intermediates:

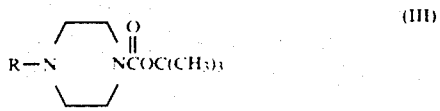

wherein R is hydrogen, benzyl or p-methoxycinnamoyl.

German Offen. No. 2,360,362 (1973) also discloses the preparation of a piperazine derivative according to formula (III) where R is $CH_3$ for use as an intermediate in making tranquilizers, anticonvulsants or muscle relaxants. This intermediate is prepared in German Offen. No. 2,360,362 according to the following reaction scheme:

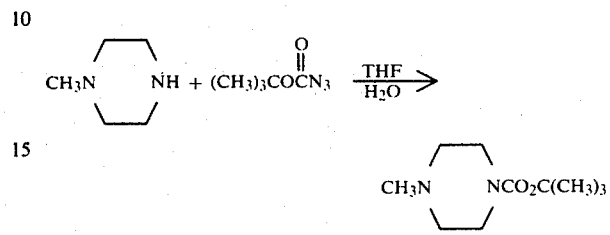

Various other esters of piperazine-1-carboxylic acids are also shown in the literature. For example, the following esters of 4-benzyl piperazine-1-carboxylic acid having the formula (IV) have been previously described:

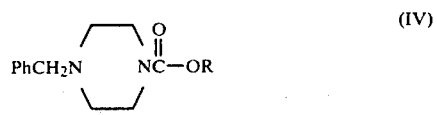

where R is (i) ethyl; (ii) —$CH_2CH_2N(C_2H_5)$; and (iii) benzyl. Compound (i) is also described as an intermediate [Canadian J. Chem., 47, 2413 (1969); J. O. C. 13, 134 (1948); J. Amer. Chem. Soc., 77, 753 (1955); Chem. Abs., 51, P 1308C] and compound (ii) is disclosed as a pharmaceutical [Chem. Abs., 48, P 2124C] and as a potential antiviral [J. Med. Chem., 11, 720 (1968)]. Compound (iii) is also disclosed as an intermediate in Chem. Abs., 50, P 10138f.

Notwithstanding the relatively extensive literature regarding esters of piperazine carboxylic acids, many of the compounds of formula (I) are new per se. Accordingly, another feature of the invention is the provision of novel piperazine derivatives of the formula (V):

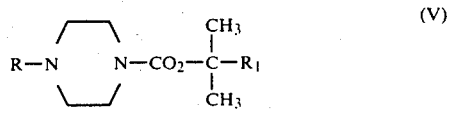

wherein R has the meaning hereinafter described and $R_1$ is $CH_3$, $C\equiv CH$ or $CH=CH_2$ with the proviso that when $R_1$ is $CH_3$, R has a value other than hydrogen, $CH_3$, benzyl and p-methoxycinnamoyl.

According to a further feature of the invention there is provided a pharmaceutical composition which comprises, as active ingredient, an effective amount of a piperazine derivative of formula (I) in association with a non-toxic, pharmaceutically-acceptable diluent or carrier. The pharmaceutical composition may be in a form suitable for oral, parenteral or rectal administration. For example, the composition may be formulated by means known to the art into tablets, capsules, aqueous or oily solutions, suspensions or emulsions, or sterile injectable aqueous or oily solutions or suspensions, dispersible powders or suppositories.

Pharmaceutical compositions according to the invention may also contain, in addition to the active piperazine derivative, one or more known drugs, e.g. other analgesic or antidepressant agents such as aspirin, paracetamol, phenacetin, codeine, meperidine and morphine; anti-inflammatory agents, for example, naproxen, indomethacin and ibuprofen; and neuroleptic agents such as chlorpromazine, prochlorperazine, trifluoperazine and haloperidol.

Preferred pharmaceutical compositions of the invention include one suitable for oral administration in unit dosage form, for example, tablets and capsules which may contain between 1 and 200 mg. of the active ingredient, or one suitable for intravenous, intramuscular or subcutaneous injection, for example, a sterile aqueous solution containing between 1 and 50 mg./ml. of active ingredient. Obviously, however, the amount of active ingredient utilized will be varied depending on, for example, the degree of activity of the piperazine derivative involved.

The R substituent in the compounds represented by formulas (I) and (V) can be fairly widely varied as this portion of the molecule seems to be relatively tolerant to substitution. Thus R may be selected from the group consisting of hydrogen, hydroxy, optionally substituted lower alkyl, lower alkenyl or lower alkynyl, cycloalkyl, acyl, acyloxy, alkoxy, alkoxycarbonyl, aralkyloxy, aryl, aralkyl, or 5- or 6-membered heterocyclic wherein the heterocyclic ring includes one or two —N— atoms.

As representative alkyl values for R there may be mentioned straight or branched chain alkyl of 1–6 carbons, preferably 1–4, e.g. methyl, ethyl, n-propyl, isopropyl, n-butyl, isobutyl, pentyl, etc. Such alkyl may be unsubstituted or substituted. Typical examples of substituted alkyl which are contemplated include:

(a) mono- and di- hydroxyalkyl or mono-cyanoalkyl of 1–4 carbon atoms, e.g.
HOCH$_2$CH$_2$—,
HOCH$_2$CHOHCH$_2$—,
CH$_3$CHOHCH$_2$—,
HOCH$_2$CHOCH$_2$CH$_2$—
NCCH$_2$CH$_2$CH$_2$—,
NCCH$_2$CH$_2$— or the like;

(b) methyl or ethyl sulfonyl or sulfinyl alkyl of 1–3 carbons, e.g.

CH$_3$CH$_2$SO$_2$CH$_2$CH$_2$—or CH$_3$SCH$_2$CH$_2$—;
O (c) amidoalkyl or aminocarbonylalkyls wherein the alkyl contains 1–4 carbons and mono- and di- N-methyl or N-ethyl or N-cyclohexyl substituted aminocarbonylalkyl, e.g.

H$_2$NCOCH$_2$—

H$_2$NCOCH$_2$CH$_2$—

Et NCOCH$_2$—
|
H

H$_2$NCOCHCH$_2$—
|
CH$_3$

Me$_2$NCOCH$_2$CH$_2$— or

MeNCOCH$_2$CH$_2$—
|
H

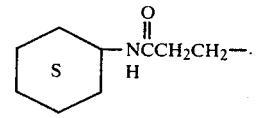

(d) carbonatoalkyl (C$_2$ to C$_4$) (e.g. C$_6$H$_5$OCO$_2$CH$_2$CH$_2$—), (e) carbamatoalkyl wherein the alkyl contains 1–3 carbons (e.g. H$_2$NCOOCH$_2$CH$_2$), (f) oxoalkyl wherein the alkyl contains 1–3 carbons, e.g.

2-propanone CH$_3$CCH$_2$—, 2-butanone CH$_3$ C CH$_2$ CH$_2$—
‖ ‖
O O or 3-butanone CH$_3$ CH$_2$ C CH$_2$—
‖
O (g) hetero-substituted methyl or ethyl wherein the hetero substituent is, for example, a 1- or 2-thienyl; 2-, 3- or 4-pyridyl; 3-(1-methyl-indolyl); uracil or 4-oxazolidin-2-one; and (h) N-succinimidoalkyl wherein the alkyl contains 1–3 carbon atoms, e.g.

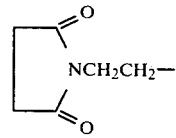

Representative lower alkenyl (C$_3$ or C$_4$) and alkynyl (C$_3$ or C$_4$) values for R include 1- and 2-propenyl; 1- and 2-propynyl; 1-, 2- or 3-butynyl; phenylalkenyl (C$_3$ or C$_4$ for example 1-phenyl-2-propenyl C$_6$H$_5$CH=CHCH$_2$ and the like.

Examples of cycloalkyl substituents suitable for R include those containing from 3–6 carbons, e.g. cyclopropyl, cyclopentyl and cyclohexyl.

As representative acyl substituents for R there may be mentioned acyl containing a C$_1$ to C$_4$ alkyl, e.g. acetyl, propionyl or trifluoroacetyl or aroyl, e.g. benzoyl. Typical acyloxy substituents include those containing acyl of the type just listed.

When R is alkoxy, this may contain up to 4 carbon atoms, e.g. methoxy, ethoxy, propoxy, butoxy. Suitable aralkoxy substituents for R include benzyloxy. As a typical alkoxycarbonyl there may be mentioned

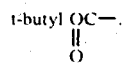

Suitable aryl values for R include unsubstituted or substituted phenyl or naphthyl, e.g. mono- or di-alkyl ($C_1$ or $C_2$)- or mono to tri-halo (Cl,Br,I or F)-substituted phenyl or naphthyl.

Representative heterocyclic values for R include N-unsubstituted and N-aryl or N-alkyl ($C_1$–$C_3$) substituted 3-succinimido, e.g.

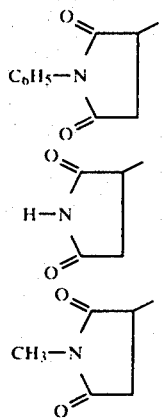

As other heterocyclic R values, there may be mentioned pyrimidyl, pyridinyl or pyrrolid-2- ones, for example:

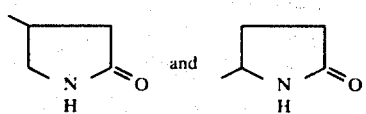

Representative aralkyl values for R include 1- and 2-phenethyl, benzhydryl, 1-naphthyl, benzyl and benzyl mono- or di-substituted with chlorine, fluorine, methyl, acetoxy, hydroxy, methoxy or benzyloxy such as m—$CF_3C_6H_4CH_2$—
m—$CH_3OC_6H_4CH_2$—
m—$ClC_6H_4CH_2$—
o—$ClC_6H_4CH_2$—
p—$ClC_6H_4CH_2$—
p—$CH_3C_6H_4CH_2$—
p—$FC_6H_4CH_2$—
p—$(C_6H_5CH_2O)C_6H_4CH_2$—
p—$HOC_6H_5CH_2$—

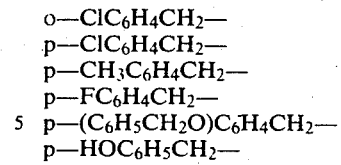

Specific compounds for use according to the invention are illustrated in the working examples which are set forth hereinafter. It will be appreciated that the antidepressant and analgesic activity of these compounds and others embraced by formula (I) will vary over a fairly wide range from a relatively low degree of antidepressant and/or analgesic activity to a relatively high degree of activity.

A preferred subgroup of compounds of formula (I) which demonstrate a particularly high degree of activity are those where $R_1$ is $CH_3$ and R is selected from the group consisting of lower alkoxy (especially methoxy); hydroxyalkyl (notably hydroxyethyl); methylsulfinyl alkyl, especially 2-(methylsulfinyl) ethyl; cyanoalkyl (notably cyanoethyl); aminocarbonylalkyl (wherein the alkyl is methyl or ethyl and the amino nitrogen is unsubstituted or substituted with alkyl); or 4- or 5-pyrrolid-2-ones. A preferred compound within this subgroup is that where R is 2(aminocarbonyl) ether and $R_1$ is $CH_3$. This compound (hereinafter referred to as Compound A for ease of reference) demonstrates a particularly effective combination of antidepressant and analgesic activity in standard experimental tests, the antidepressant activity being comparable with Imipramine, as well known antidepressant agent extensively used in humans. Compound A has a high therapeutic ratio and has shown no undesirable side-effects, including no anticholinergic effects.

Other specific compounds which are preferred are those wherein $R_1$ is $CH_3$ and R is —$OCH_3$, 2-(methylsulfinyl) ethyl or 5-pyrrolid-2-one.

The compounds of formula (I) may be prepared using conventional methods known in the art for preparing piperazine 1-carboxylates. The following different preparation methods are illustrated in Examples 1–18, it being noted that of these methods, 1(c) and 1(d) are believed to be specifically novel when used in the preparation of piperazine-1-carboxylates:

Method I

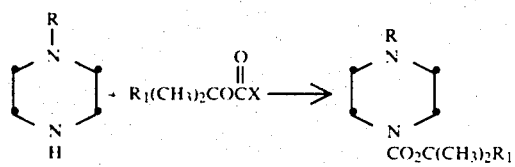

|  | X | $R_1$ |
|---|---|---|
| Method Ia | —Cl | —C≡CH |
| Ib | —$N_3$ | —$CH_3$ |
| Ic | —ON=(CN)$CC_6H_5$ | —$CH_3$ |
| Id | —$OC_6H_5$ | —$CH_3$, —CH≡CH, —CH=$CH_2$ |

Method II

-continued
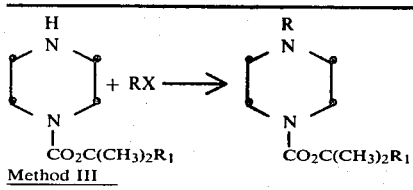
Method III
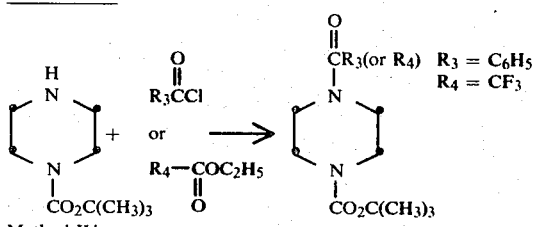
Method IV
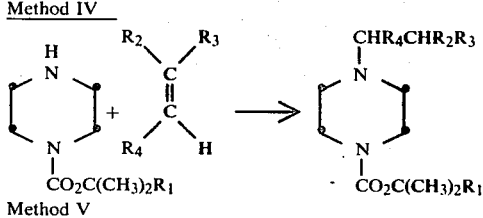
Method V
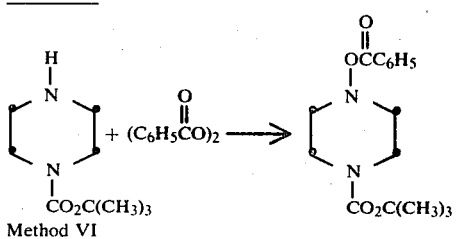
Method VI
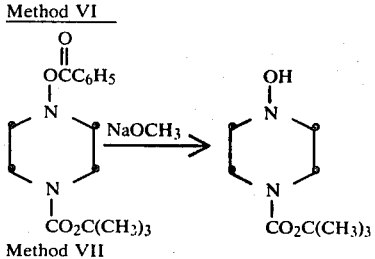
Method VII
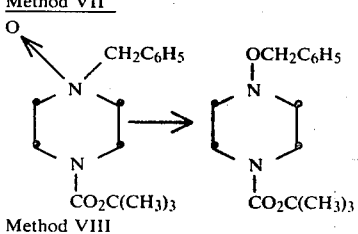
Method VIII
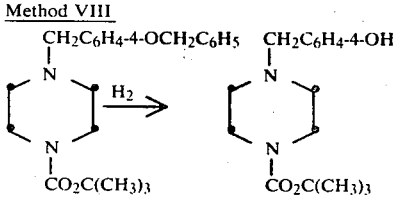
Method IX
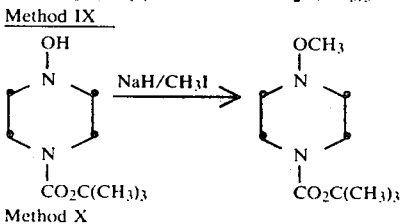
Method X

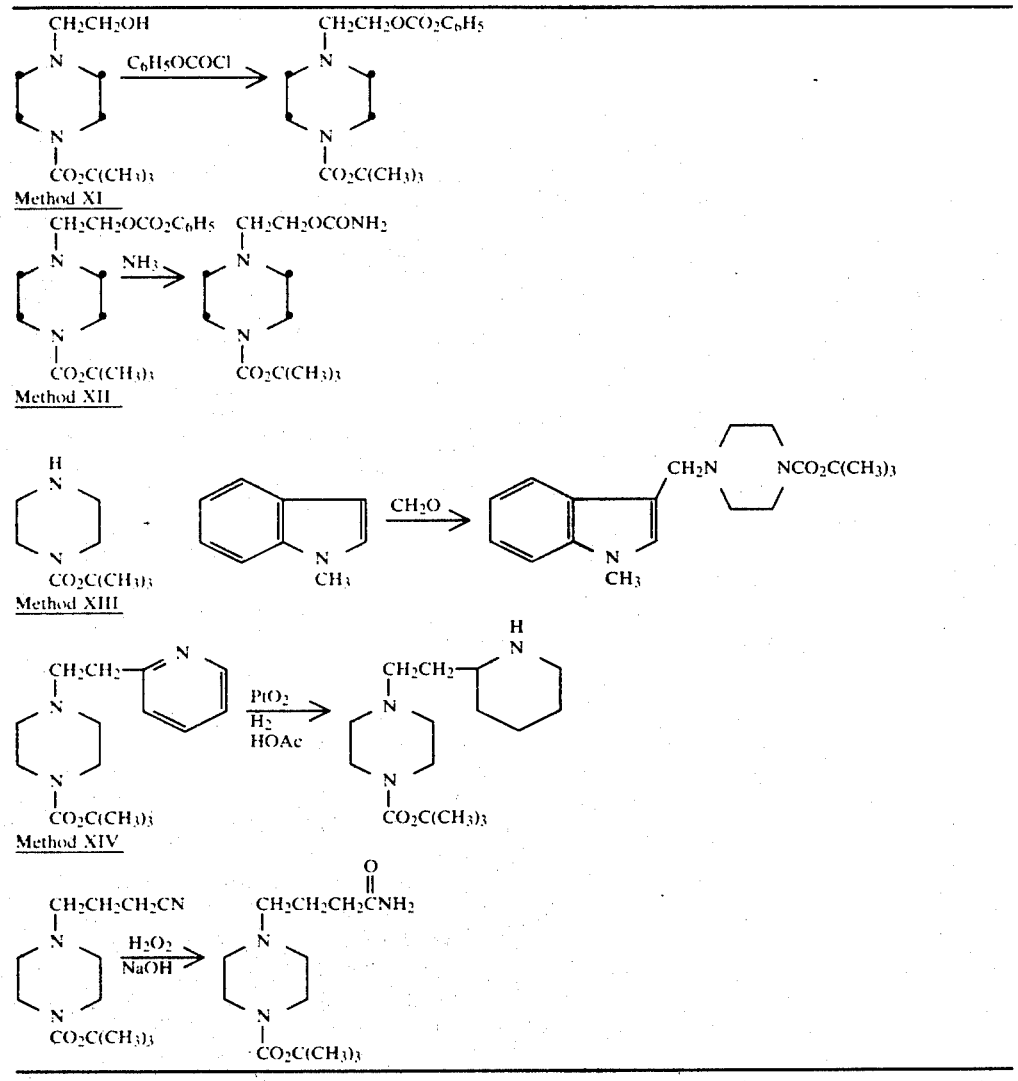

The invention is illustrated, but not limited, by the following examples wherein temperatures are expressed in centigrade:

EXAMPLE 1

Method 1a

Synthesis of 1-methyl-4-(1,1-dimethyl-2-propynoxycarbonyl)piperazine hydrochloride

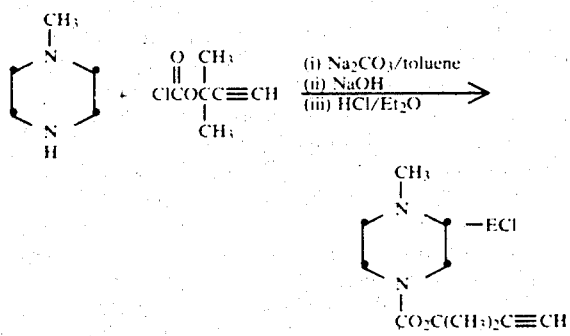

A solution of 5.9 g (0.04 mole) of 1,1-dimethyl-2-propynoxycarbonyl chloride, which was prepared according to a procedure described in J. Org. Chem. 35 3291 (1970), in 15 ml of toluene was rapidly added from a dropping funnel to a stirred, cooled (ice-bath) mixture of 4.0 g (0.04 mole) of 1-methylpiperazine, 4.3 g (0.04 mole) of sodium carbonate and 25 ml of toluene. The temperature rose rapidly to 40° and then fell. The mixture was stirred for 1 additional hour in the ice-bath and then at room temperature overnight. Aqueous sodium hydroxide (5%, 20 ml) was then added and the layers separated. The aqueous phase was extracted with two 25 ml portions of ethyl ether, the organic phases combined and dried (MgSO₄). Filtration and evaporation of the solvent gave 3.9 g (46%) of orange oil. The oil was dissolved in ethyl ether and treated with an ethereal solution of anhydrous hydrochloric acid. The resulting brown solid was filtered off, dissolved in 60 ml of hot absolute ethanol, treated with Darco and filtered to yield a yellow solution. Treatment with 140 ml of 30–60 petroleum ether and refrigeration yielded 2.8 (28%) of white solid, mp-212-4° dec. Calc. for $C_{11}H_{19}ClN_2O_2$ (246.74): C, 53.35; H, 7.76; N, 11.35, Cl, 14.37. Found: C, 53.67; H, 7.88; N, 11.41; Cl, 14.60.

EXAMPLE 2

Method Ib

Synthesis of 1-(1,1-dimethylethoxycarbonyl)4-phenylmethylpiperazine

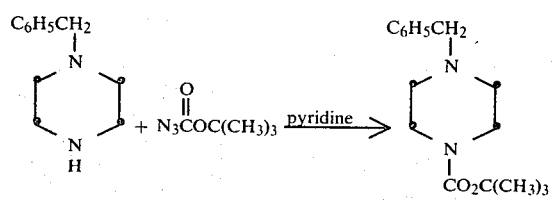

A solution of 3.4 g (0.024 mole) of 1,1-dimethylethoxy carbonylazide in 5 ml of pyridine was rapidly added to a stirred solution of 1-phenylmethylpiperazine (4.2 g, 0.024 mole) in 5 ml of pyridine. An initial exothermic reaction was noted. The mixture was allowed to stir overnight, diluted with water and the product was extracted with two 50 ml portions of ether. The ether extracts were dried (MgSO$_4$), filtered, and evaporated to yield a yellow oil. Column chromatography (2" diameter column, 500 g of silica gel, ether eluent) followed by sublimation at 110°/0.5 mm returned 5.7 g (86%) of white solid, m.p. 64°-73°. The solid was dissolved in 50 ml of ether and cooled to −70°. The resultant white solid was filtered off to yield 4.5 g (68%) of product, m.p. 71-3°. Calc. for C$_{16}$H$_{24}$N$_2$O$_2$ (276.38): C, 69.53; H, 8.75; N, 10.14. Found: C, 69.44; H, 8.82; N, 10.15.

EXAMPLE 3

Method Ic

Synthesis of 1-cyclopropyl-4-(1,1-dimethylethoxycarbonyl)piperazine

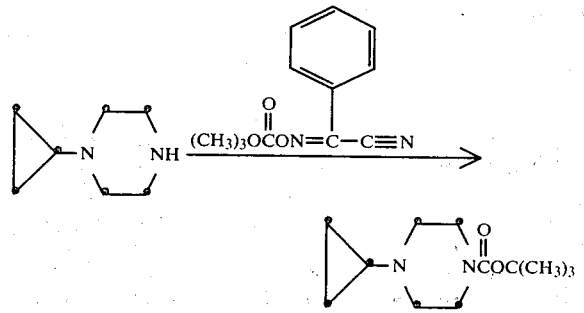

Solid 2-(t-butoxycarbonyloxyimino)-2-phenylacetonitrile (3.2 g, 0.013 mole) was added in one portion to a solution of 1.5 g (0.012 mole) 1-cyclopropylpiperazine in 30 ml ethyl acetate. The solution was stirred at room temperature for 3 hours and then treated with 100 ml dilute aqueous HCl. The aqueous phase was separated, extracted with additional ethyl acetate (discarded), treated with excess 10% NaOH, and extracted with ether. The ether extracts were dried (MgSO$_4$), filtered, and evaporated in vacuo to yield a semi-solid residue. Recrystallization from hexane at −70° C. gave 1.9 g white, crystalline solid, m.p. 65°-67° C. Calculated for C$_{12}$H$_{22}$N$_2$O$_2$ (226.32): C, 63.98; H, 9.80; N, 12.38; O, 14.14. Found: C, 63.82; H, 9.82; N, 12.60; O, 13.90.

EXAMPLE 4

Method Id

Synthesis of 1-(1,1-dimethylpropynoxycarbonyl)piperazine

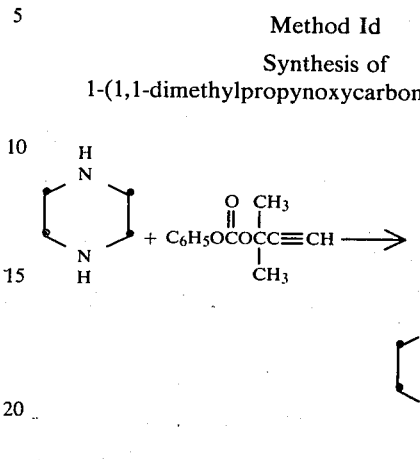

A stirred mixture of 25.8 g (0.3 mole) of piperazine and 30.6 (0.15 mole) of 1,1-dimethylpropynoxyphenyl carbonate was heated at 90° for 18 hrs. The reaction mixture was cooled and partitioned between excess 5% NaOH solution and 100 ml of CH$_2$Cl$_2$. The layers were separated and the water layer extracted twice more with 100 ml portions of CH$_2$Cl$_2$. The organic extracts were dried (MgSO$_4$), filtered and evaporated to an orange oil. Distillation through a 4-inch Vigreaux column gave 18.3 g (62%) of light yellow oil which solidified on standing, m.p. 35°-8°. The hydrochloride salt prepared in ether and recrystallized from acetonitrile had a m.p. of 193°-4° dec. Calc. for C$_{10}$H$_{17}$ClN$_2$O$_2$ (232.71): C, 51.61; H, 7.36; Cl, 15.23; N, 12.04. Found: C, 51.37; H, 7.39; Cl, 15.19; N, 11.92.

The 1,1-dimethylpropynoxyphenyl carbonate used herein was prepared as follows:

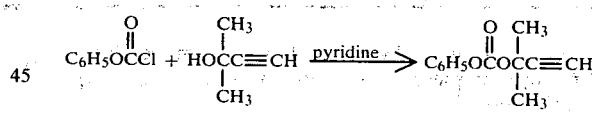

To a mechanically stirred, cooled (ice-bath) solution of 25.2 g (0.3 mole) of 1,1-dimethylpropynol in 120 ml of dry pyridine was added dropwise at such a rate as to keep the temperature below 10° 47.0 g (0.3 mole) of phenylchloroformate. After stirring at room temperature overnight the mixture was treated with 300 ml of cold water and extracted with three 100 ml portions of ether. The combined extracts were washed successively with two 100 ml portions 2NHCl, two 150 ml portions of 5% NaOH and finally saturated NaCl solution. The organic phase was dried (MgSO$_4$), filtered and the ether removed in vacuo. Distillation through a 4-inch Vigreaux column gave 56.0 g (92%) of colorless oil, b.p. 83.5°-86°/0.35 mm. Calc. for C$_{12}$H$_{12}$O$_3$ (204.23): C, 70.58; H, 5.92. Found: C,70.51; H, 5.83.

1,1-dimethylpropenoxyphenyl carbonate for use in preparing the corresponding piperazine where R$_1$ is —CH=CH$_2$ rather than —C≡CH was synthesized in the same way as the propynoxy counterpart, as follows:

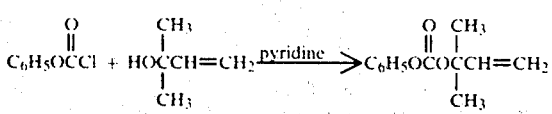

The yield of 1,1-dimethylpropenoxyphenyl carbonate was 92% of colorless oil, b.p. 85°–90°/0.5 mm. Calc. for $C_{12}H_{14}O_3$ (206.24): C, 69.89; H, 6.84. Found: C, 69.88; H, 6.70.

Tert-butylphenyl carbonate for use in preparing the corresponding piperazine where $R_1$ is $CH_3$ is commercially available (Aldrich Chemical Co.).

EXAMPLE 5

Method II

Synthesis of 1-(1,1-dimethylethoxycarbonyl)-4-(2-oxopropyl)piperazine hydrochloride.

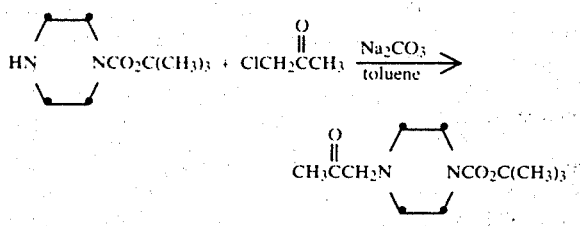

A mixture of 2.7 ml (0.03 mole) of 90% chloro-2-propanone, 5.6 g (0.03 mole) of 1,1-dimethylethoxycarbonylpiperazine, 3.7 g (0.03 mole) of sodium carbonate hydrate and 30 ml of toluene was stirred at 100° for 5 hours and then at room temperature overnight. The reaction mixture was then treated with 10% NaOH solution and the layers separated. The toluene layer was washed twice with water, dried (MgSO$_4$), filtered and concentrated in vacuo to yield 6.2 g of orange oil. Distillation through a 4-inch Vigreaux column returned 5.0 g (68%) of colorless oil, b.p. 115°–7°/0.3 mm. The white hydrochloride salt, prepared in ether and recrystallized from iPrOH-Et$_2$O, weighed 5.5 g (66%), m.p. 164°–6° dec. Calc. for $C_{12}H_{23}ClN_2O_3$ (278.78): C, 51.70; H, 8.32; Cl, 12.72; N, 10.05. Found: C, 51.66; H, 8.22; Cl, 12.89; N, 9.96.

EXAMPLE 6

Method III

Synthesis of 1-trifluoroacetyl-4-[1,1-dimethylethoxycarbonyl]piperazine.

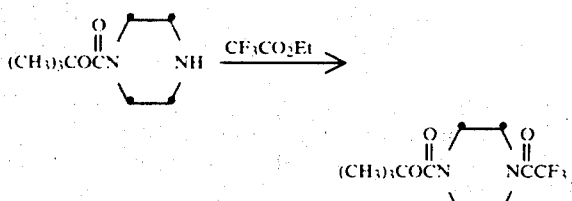

Ethyl trifluoroacetate (3.9 g, 0.027 mole) was added over 10 minutes to a warm (40° C.) stirred melt of 5.2 g (0.028 mole) 1-[1,1-dimethylethoxycarbonyl]piperazine. The mixture was heated at 120° C. for 2 hours, cooled to room temperature, treated with 1.0 g (0.007 mole) ethyl trifluoroacetate, and reheated for an additional 2 hours. The mixture was allowed to stand 18 hours at room temperature and then was evaporated in vacuo. The residue was dissolved in ether, passed through an alumina-packed column (2.2×16 cm), the eluent collected, washed with dilute aqueous HCl, dried (MgSO$_4$), filtered, and evaporated in vacuo to yield 6.6 g yellow oil which solidified on standing. Recrystallization from hexane gave 6.0 g of white, crystalline solid, m.p. 66°–68° C. Calc. for $C_{11}H_{17}F_3N_2O_3$ (282.26): C, 46.81; H, 6.07; N, 9.92. Found: C, 46.76; H, 6.40; N, 10.12.

EXAMPLE 7

Method III

Synthesis of 1-benzoyl-4-(1,1-dimethylethoxycarbonyl)piperazine.

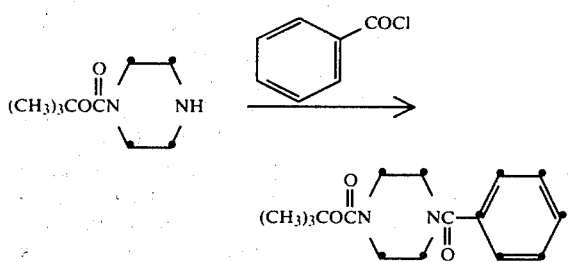

A mixture of 2.5 g (0.013 mole) of 1,1-dimethylethoxycarbonylpiperazine, 2.0 g (0.014 mole) of benzoyl chloride, 2.25 g (0.027 mole) of sodium bicarbonate and 100 ml of toluene was stirred at reflux overnight. The mixture was cooled, filtered and evaporated in vacuo to yield 3.85 g (100%) of white solid, m.p. 105.5°–106.5°. Calc. for $C_{16}H_{22}N_2O_3$ (290.36): C, 66.18; H, 7.64; N, 9.65. Found: C, 66.24; H, 7.51; N, 9.64.

EXAMPLE 8

Method IV

Preparation of 1-(3-amino-3-oxopropyl)-4-(1,1-dimethylethoxycarbonyl)piperazine.

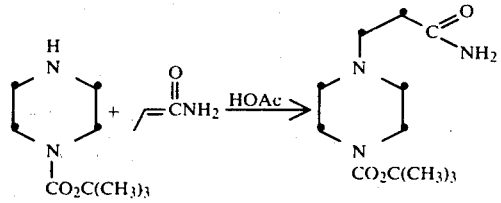

A molten mixture of 7.5 (0.04 mole) of 1-(1,1-dimethylethoxycarbonyl)piperazine, 2.9 g (0.04 mole) of acrylamide and 3 drops of acetic acid was stirred and heated at 65° for 18 hours. The mixture which had solidified during the heating period was dissolved in 100 ml of chloroform and washed with dilute aqueous sodium hydroxide solution. The dried (MgSO$_4$) CHCl$_3$ solution was filtered and evaporated in vacuo to yield a white solid. Recrystallization from toluene-hexane returned 8.0 g (78%) of product, m.p. 96°–8°. Calc. for $C_{12}H_{13}N_3O_3$ (257.335): C, 56.01; H, 9.01; N, 16.33. Found: C, 56.05; H, 9.04; N, 16.05.

EXAMPLE 9

Method V

Synthesis of 1-benzoyloxy-4-(1,1-dimethylethoxycarbonyl)piperazine.

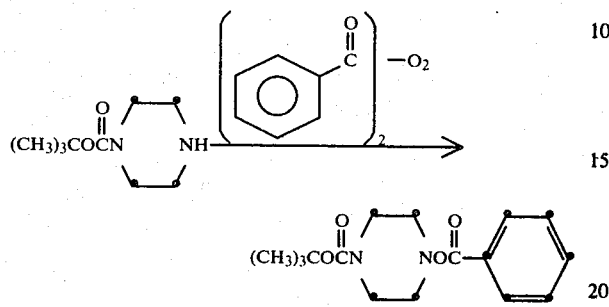

A solution of 13 g (0.054 mole) benzoyl peroxide in 500 ml ether was added dropwise over 6 hours to a refluxing solution of 10 g (0.054 mole) 1-(1,1-dimethylethoxycarbonyl) piperazine in 500 ml ether. The solution was refluxed for 18 hours and then 0.5 g (0.0027 mole) 1-(1,1-dimethylethoxycarbonyl) piperazine in ether was added over 3 hours. The solution was stirred for 18 hours at room temperature, washed successively with 5% aqueous Na$_2$CO$_3$, dilute aqueous HCl, 5% aqueous Na$_2$CO$_3$, and H$_2$O. The solution was dried (MgSO$_4$), filtered, and evaporated in vacuo to give 17.3 g of solids. Recrystallization from ether-hexane gave 10.2 g off-white solid, m.p. 105°–107° C. Calc. for C$_{16}$H$_{22}$N$_2$O$_4$ (306.36): C, 62.73; H, 7.24; N, 9.14; O, 20.89. Found: C, 62.82; H, 7.01; N, 8.98; O, 21.30.

EXAMPLE 10

Method VI

Synthesis of 1-hydroxy-4-(1,1-dimethylethoxycarbonyl) piperazine.

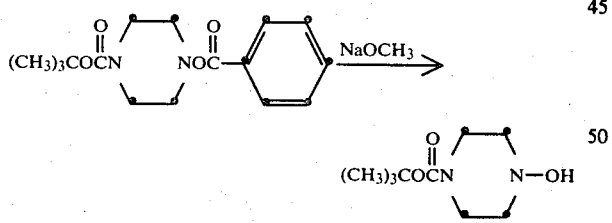

A solution of 3.8 g (0.012 mole) 1-benzoyloxy-4-[1,1-dimethylethoxycarbonyl]piperazine in 25 ml methanol-ether (1:1) was added dropwise to a stirred suspension of 0.95 g (0.017 mole) sodium methoxide in 25 ml methanol at room temperature. The mixture was stirred for 2 hours, treated with 50 ml H$_2$O, and evaporated in vacuo. The residue was thoroughly extracted with ether and the extracts were dried (MgSO$_4$), filtered, diluted with hexane, and evaporated to a lower volume to yield 1.9 white, crystalline solid, m.p. 95°–97° C. Calc. for C$_9$H$_{18}$N$_2$O$_3$ (202.25): C, 53.45; H, 8.97; N, 13.85; O, 23.73. Found: C, 53.26; H, 8.74; N, 13.98; O, 23.96.

EXAMPLE 11

Method VII

Synthesis of 1-(1,1-dimethylethoxycarbonyl)-4-phenylmethoxypiperazine.

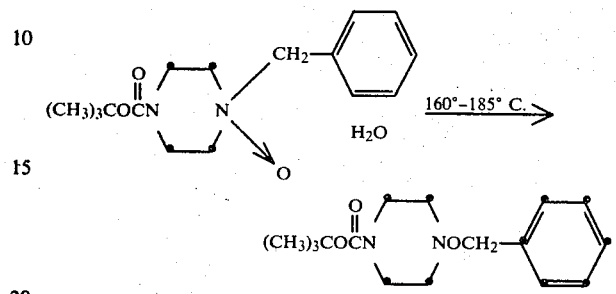

A flask containing 10.4 g (0.034 mole) 1-[1,1-dimethylethoxycarbonyl]-4-phenylmethylpiperazine-4-oxide hydrate was slowly heated, under reduced pressure, to 160° C. over a 4-hour period. The temperature was increased to 170°–185° C. and 8.5 g distillate, b.p. 135°–140° C./0.15–0.20 mm was collected. Redistillation returned 7.2 g colorless oil, b.p. 140°–141° C./0.15–0.20 mm. The oil was dissolved in ether-hexane (1:1) and passed through an alumina-packed column (2.2×16 cm). The eluent was collected, evaporated in vacuo, dissolved in ether, washed with dilute aqueous HCl, dried (MgSO$_4$), filtered and evaporated in vacuo. Recrystallization from low boiling (35°–65° C.) petroleum ether at −70° C. gave 6.1 g white, crystalline solid, m.p. 59°–61° C. Calc. for C$_{16}$H$_{24}$N$_2$O$_3$ (292.38): C, 65.73; H, 8.27; N, 9.58; O, 16.42. Found: C, 65.47; H, 8.20; N, 9.57; O, 16.55.

The 1-(1,1-dimethylethoxycarbonyl)-4-phenylmethylpiperazine-4-oxide hydrate used above was prepared as follows:

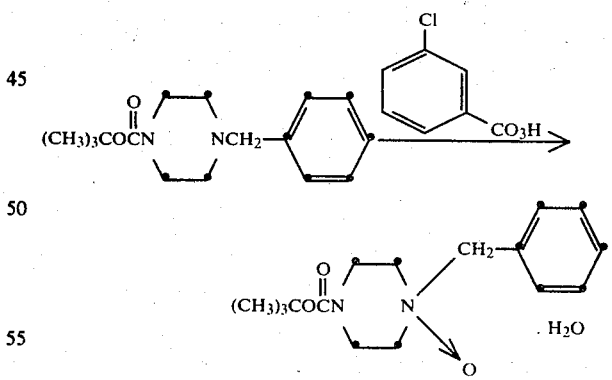

A solution of 10.0 g (0.058 mole) m-chloroperbenzoic acid in 100 ml chloroform was added over a one hour period to a cooled (0°–5° C.) solution of 16.1 g (0.058 mole) 1-[1,1-dimethylethoxycarbonyl]-4-phenylmethylpiperazine in 200 ml chloroform. External cooling was removed and the solution stirred for 96 hours at room temperature. The solution was then successively passed through four alumina-packed columns (2.2×16 cm), the eluent evaporated in vacuo, treated with 200 ml acetone and diluted with 50 ml hexane to yield 9.0 g white, crystalline solid, m.p. 123°–126° C. (sealed capillary).

An analytical sample from a prior run gave a satisfactory elemental analysis. Calc. for $C_{16}H_{29}N_2O_3 \cdot H_2O$ (310.40): C, 61.91; H, 8.44; N, 9.03; O, 20.62. Found: C, 61.91; H, 8.27; N, 9.07; O, 20.55.

EXAMPLE 12

Method VIII

Synthesis of 1-(4-hydroxyphenylmethyl)-4-(1,1-dimethylethoxycarbonyl)piperazine (Z)-2-butenedioate (1:1)

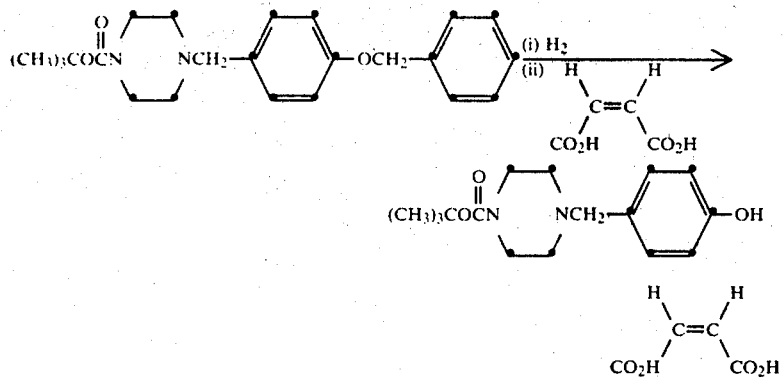

A mixture of 2.8 g (0.007 mole) 1-(1,1-dimethylethoxycarbonyl)-4-(4-phenylmethoxyphenylmethyl)piperazine, 0.15 g 10% Pd-C, and 200 ml ethanol was hydrogenated for 7 hours at room temperature and at 6 psi $H_2$ pressure. The catalyst was removed by filtration and the filtrate evaporated in vacuo to yield 2.2 g yellow-orange oil. The oil was dissolved in ether and passed through a silica-packed column (2.2 × 16 cm), the eluent collected and evaporated in vacuo to yield 1.6 g yellow oil. The oil was re-dissolved in ether, treated with 0.6 g (0.005 mole) maleic acid in ethanol, diluted with additional ether, and left to stand at room temperature. The solids were recovered by filtration, washed with ether, and vacuum dried. Recrystallization from ethanol-ether gave 1.0 g white, crystalline solid, m.p. 176°–178° C. dec. Calc. for $C_{16}H_{24}N_2O_3 \cdot C_4H_4O_4$ (408.45): C, 58.81; H, 6.91; N, 6.86; O, 27.42. Found: C, 58.99; H, 6.84; N, 6.82; O, 27.33.

EXAMPLE 13

Method IX

Synthesis of 1-methoxy-4-(1,1-dimethylethoxycarbonyl) piperazine.

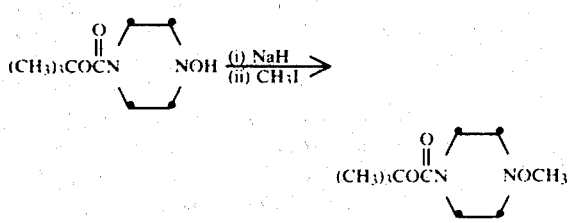

A 57% oil dispersion containing 0.6 g (0.025 mole) NaH was added in one portion to a solution of 4.7 g (0.023 mole) 1-hydroxy-4-(1,1-dimethylethoxycarbonyl)piperazine in 100 ml DMF under a dry $N_2$ atmosphere. The mixture was stirred for 2 hours at room temperature and then 6.5 g (0.046 mole) iodomethane was added over 1 minute. After stirring for an additional 15 minutes, the mixture was poured into 100 ml $H_2O$, stirred briefly, and extracted thoroughly with low boiling (35°–65° C.) petroleum ether. The extracts were dried (MgSO$_4$), filtered and evaporated in vacuo to give 1.8 g of an oil. The oil was dissolved in ethyl ether, washed with dilute aqueous HCl, dried (MgSO$_4$), filtered, and evaporated in vacuo to yield 1.3 g yellow oil. Short path distillation (Kugelrohr) returned 0.8 g colorless distillate, b.p.* 55°–65° C./0.15 mm. Calc. for $C_{10}H_{20}N_2O_3$ (216.28): C, 55.53; H, 9.32; N, 12.95; O, 22.19. Found: C, 55.61; H, 9.13; N, 12.96; O, 22.33.

*Temperature range of radiant heat oven over which distillate was collected.

EXAMPLE 14

Method X

Synthesis of 1-(1,1-dimethylethoxycarbonyl)-4-[2-(phenyloxycarbonyloxy)ethyl]piperazine hydrochloride.

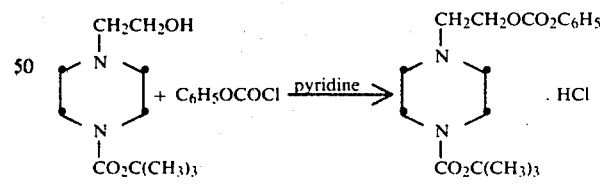

To a stirred, cooled (ice-bath) solution of 15.0 g (0.065 mole) 1-(2-hydroxyethyl)-4-(1,1-dimethylethoxycarbonyl) piperazine in 100 ml of pyridine was slowly added 10.2 g (0.065 mole) of phenylchloroformate at such a rate as to maintain the temperature at 15°. The ice-bath was then removed and the mixture allowed to stir at 30° for 2 hours. Ether (100 ml) was added and the resulting white precipitate was collected by filtration, ground with water in a blender, refiltered, washed with additional water and air dried to yield 5.3 g (25%) of white solid, m.p. 203.5°–204°. Calc. for $C_{18}H_{26}N_2O_5 \cdot HCl$ (385.87): C, 56.02; H, 6.79; N, 7.26; Cl, 9.19. Found: C, 56.25; H, 6.59; N, 7.08; Cl, 9.12.

EXAMPLE 15

Method XI

Synthesis of 1-[2-(aminocarbonyloxy)ethyl]-4-(1,1-dimethylethoxycarbonyl)piperazine.

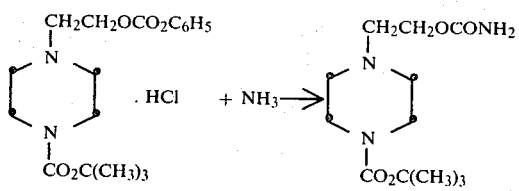

1-(1,1-dimethylethoxycarbonyl)-4-[2-(phenyloxycarbonyloxy)ethyl]piperazine hydrochloride (3.5 g., 0.009 mole) was treated with 50 ml of 10% NaOH solution and the free base extracted with ether. The ether extracts were dried (MgSO$_4$), filtered and treated with 50 g of ammonia. After 2 hours at reflux the ammonia and ether were removed and the residue recrystallized from 200 ml of ether to yield 2.0 g (81%) of white crystals, m.p. 135°–6.5°. Calc. for $C_{12}H_{23}N_3O_4$ (273.32): C, 52.73; H, 8.48; N, 15.37. Found: C, 52.87; H, 8.25; N, 15.46.

EXAMPLE 16

Method XII

Synthesis of 1-(1,1-dimethylethoxycarbonyl)-4-[(1-methylindol-3-yl)methyl]piperazine [Z]-2-butenedioate (1:1)

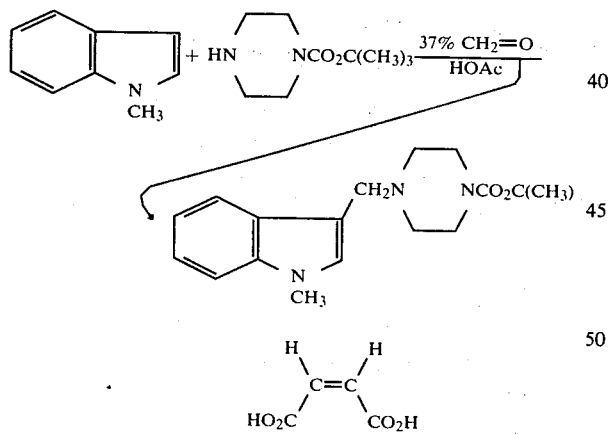

To a stirred cooled (10°, ice bath) solution of 3.9 g (0.03 mole) of 1-methylindole and 5.6 g (0.03 mole) of 1-(1,1-dimethylethoxy carbonyl)piperazine in 20 ml of acetic acid was added dropwise 2.4 g (0.03 mole) of a 37% aqueous solution of formaldehyde. The ice bath was removed and the mixture allowed to stir at room temperature overnight. The mixture then treated with 200 ml of 10% NaOH solution and extracted with two 100 ml portions of Et$_2$O. The combined extracts were dried (MgSO$_4$), filtered and evaporated in vacuo. The resulting oil was chromatographed on a 4.5 cm diameter column using 100 g of Grace #923 silica gel as absorbent and EtOAc as elutent. The proper fractions were combined and evaporated in vacuo to yield 8.4 g (85%) of colorless oil. The [Z]-2-butenedioate prepared in Et$_2$O and recrystallized from CH$_3$OH/Et$_2$O had a mp of 142°–4°. Calc for $C_{23}H_{31}N_3O_6$(445.519): C, 62.01; H, 7.01; N, 9.43. Found: C, 63.93; H, 7.18, N, 9.18.

EXAMPLE 17

Method XIII

Synthesis of 1-(1,1-dimethylethoxycarbonyl)4-[Z-(2-piperidinyl)ethyl]piperazine (Z) butenedioate (1:2)

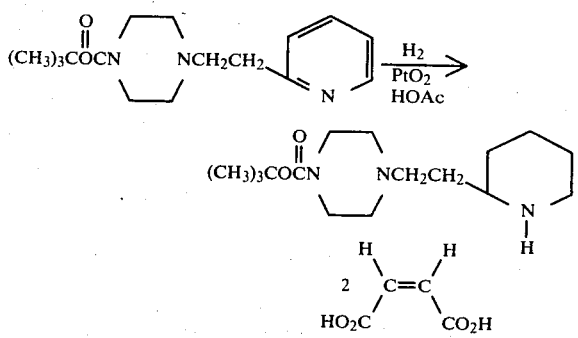

A mixture of 6.0 g (0.021 mole) of 1-(1,1-dimethylethoxy carbonyl)-4-[2-(2-pyridinyl)ethyl]piperazine, 1.5 g PtO$_2$ and 100 ml acetic acid was hydrogenated on a Parr apparatus at 53 psi for 2.5 hours during which time a theoretical amount of hydrogen was absorbed. The mixture was filtered through "Super-cel" to remove the catalyst and the filtrate evaporated in vacuo to yield 5.9 g (96%) viscous oil. The di (Z)-2-butenedioate salt, prepared in Et$_2$O, melted at 184°–4.5°.

Calc for $C_{24}H_{39}N_3O_{10}$(529.57): C, 54.43; H, 7.42; N, 7.93. Found: C, 54.21; H, 7.32; N, 7.95.

EXAMPLE 18

Synthesis of 1-(4-amino-4-oxobutyl)-4-(1,1-dimethyl ethoxycarbonyl)piperazine

A stirred mixture of 5.0 g (0.02 mole) of 1-(3-cyanopropyl)-4-(1,1-dimethylethoxycarbonyl)piperazine, 10 ml of 30% hydrogen peroxide solution and 10 ml of 20% NaOH solution warmed spontaneously to 42°. After the initial exothermic reaction had subsided and the temperature returned to room temperature, 50 ml of methanol was added dropwise; a temperature rise to 38° was noted. After heating two hours at 50° the mixture was diluted with 50 ml of water and extracted with CH$_2$Cl$_2$. The organic extracts were dried (Mg SO$_4$), filtered and evaporated on a rotary evaporator. The crude product was recrystallized from ethyl acetatehexane to yield 0.4 g (7%) of 1-(4-amino-4-oxobutyl)-4-(1,1-dimethylethoxycarbonyl)piperazine, ¼ hydrate, mp-67.5°–71.5°. Calc. for $C_{13}H_{15}N_3O_3$. ¼ H$_2$O (275.87): C, 56.60; H, 9.32; N, 15.23. Found: C, 56.58; H, 9.41; N, 15.23.

Further examples of the preparation of compounds of formula (I) where R$_1$ is CH$_3$ are shown in Table 1, R in each instance having the value shown.

Table 1

| R | Acid Salt | Yield (%) | M.P. or B.P. (mm) °C. | Calculated (%) C | H | N | (Other) | Found (%) C | H | N | (Other) | Method Used |
|---|---|---|---|---|---|---|---|---|---|---|---|---|
| $C_6H_5CH_2$ | | 68 | 71–3 | 69.53 | 8.75 | 10.14 | | 69.44 | 8.82 | 10.15 | | Ib+(Id) |
| H | HCl | 79 | 217–9 dec | 48.54 | 8.60 | 12.58 | (Cl 15.92) | 48.48 | 8.36 | 12.52 | (Cl 16.14) | Ib+(Id) |
| m-$CF_3C_6H_4CH_2$ | HCl | 60 | 175–7 dec | 53.62 | 6.35 | 7.36 | (Cl 9.31, F 14.96) | 53.95 | 6.38 | 7.38 | (Cl 9.48, F 15.00) | II |
| m-$CH_3OC_6H_4CH_2$ | | 65 | 122–7(0.07) | 66.64 | 8.55 | 9.14 | | 66.45 | 8.38 | 9.06 | | II |
| m-$ClC_6H_4CH_2$ | HCl | 60 | 196–9 dec | 55.34 | 6.96 | 8.07 | (Cl 20.42) | 55.44 | 6.88 | 8.00 | (Cl 20.36) | II |
| $C_6H_5CH_2CH_2$ | HCl | 54 | 187–90 dec | 62.47 | 8.32 | 8.57 | (Cl 10.85) | 62.43 | 8.24 | 8.48 | (Cl 10.88) | II |
| o-$ClC_6H_4CH_2$ | HCl | 56 | 175–8 dec | 55.34 | 6.96 | 8.07 | (Cl 20.42) | 55.40 | 6.96 | 8.06 | (Cl 20.60) | II |
| $C_6H_5CH=CHCH_2$ | HCl | 36 | 202–5 dec | 63.80 | 8.03 | 8.27 | (Cl 10.46) | 63.98 | 8.06 | 8.28 | (Cl 10.71) | II |
| p-Cl $C_6H_4CH_2$ | | 42 | 70–2 | 61.83 | 7.46 | 9.01 | (Cl 11.41) | 61.88 | 7.72 | 9.02 | (Cl 11.18) | II |
| p-$CH_3C_6H_4CH_2$ | HCl | 47 | 197–9 dec | 62.47 | 8.32 | 8.57 | (Cl 10.85) | 62.56 | 8.14 | 8.62 | (Cl 10.98) | II |
| pyridyl-CH_2 | | 82 | 66–9 | 63.85 | 8.04 | 15.96 | | 63.68 | 7.78 | 15.87 | | Ib |
| $C_6H_5$ | | 93 | 68–9 | 68.67 | 8.45 | 10.68 | | 68.82 | 8.24 | 10.74 | | Ib |
| $CH_3$ | HCl | 46 | 201–3 | 50.73 | 8.9 | 11.8 | (Cl 15.0) | 50.82 | 8.83 | 11.84 | (Cl 15.12) | Id |
| $C_6H_5C(=O)-$ | | 100 | 1.05–6.5 | 66.18 | 7.64 | 9.65 | | 66.24 | 7.51 | 9.64 | | III |
| $(C_6H_5)_2CH$ | | 74 | 130.5–1.5 | 74.96 | 8.01 | 7.95 | | 74.92 | 8.29 | 8.04 | | II |
| thienyl-$CH_2$ | HCl | 79 | 193–4 | 52.73 | 7.27 | 8.79 | (S 10.06) | 52.73 | 7.05 | 8.85 | (S 10.21) | II |
| $C_6H_5CH(CH_3)$ | | 51 | colorless oil column chromat. | 70.31 | 9.02 | 9.65 | | 70.26 | 8.71 | 9.63 | | II |
| $HOCH_2CH_2$ | HCl | 56 | 188–9 | 49.52 | 8.69 | 10.50 | (Cl 13.29) | 49.39 | 8.77 | 10.56 | (Cl 13.30) | II |
| $(CH_3)_2CH$ | HCl | 73 | 221–2 | 54.43 | 9.52 | 10.58 | (Cl 13.39) | 54.23 | 9.39 | 10.53 | (Cl 13.39) | II |
| $H_2NC(=O)CH_2$ | | 90 | 171–2 | 54.30 | 8.70 | 17.27 | | 54.15 | 8.91 | 17.25 | | II |
| thienyl-$CH_2-$ | | 44 | 68–71 | 59.54 | 7.85 | 9.92 | (S 11.35) | 59.68 | 7.71 | 9.89 | (S 11.26) | II |
| $(CH_3)_3COC(=O)$ | | 66 | 158–60 | 58.72 | 9.15 | 9.78 | | 58.82 | 9.18 | 9.86 | | Ib |
| tetrahydronaphthyl | HCl | 70 | 161–3 dec | 64.66 | 8.28 | 7.94 | (Cl 10.05) | 64.66 | 8.16 | 7.95 | (Cl 10.09) | Ib |

Table 1-continued

| R | Acid Salt | Yield (%) | M.P. or B.P. (mm) °C. | Calculated (%) C | H | N | (Other) | Found (%) C | H | N | (Other) | Method Used |
|---|---|---|---|---|---|---|---|---|---|---|---|---|
| cyclopentyl  | HCl | — | 217.5-8.5 | 57.81 | 9.36 | 9.63 | (Cl 12.19) | 57.75 | 9.20 | 9.65 | (Cl 12.00) | II |
| HO— | | 76 | 95-7 | 53.45 | 8.97 | 13.85 | | 53.26 | 8.74 | 13.98 | | VI |
| C₆H₅CH₂ (N oxide H₂O) | | 67 | 123-6 | 61.91 8.44 | 9.03 | | 61.98 | 8.27 | 9.07 | | VII | |
| C₆H₅CO— (=O) | | 63 | 105-7 | 62.73 | 7.24 | 9.14 | | 62.92 | 7.10 | 9.16 | | V |
| H₂C=CHCH₂ | HCl | 99 | 185-6 | 54.84 | 8.82 | 10.66 | (Cl 13.49) | 54.94 | 8.67 | 10.58 | (Cl 13.02) | II |
| p-FC₆H₄CH₂ | | 40 | 76-7 | 65.28 | 7.87 | 9.52 | (F 6.45) | 65.21 | 7.86 | 9.60 | (F 6.22) | II |
| HC≡CCH₂ | | 47 | 75-7(0.15) | 64.26 | 8.99 | 12.49 | | 64.39 | 9.14 | 12.67 | | II |
|  | HCl | 45 | | 51.91 | 7.04 | 18.63 | (Cl 11.79) | 51.76 | 7.13 | 18.66 | (Cl 11.73) | II |
| CH₃CH₂CH₂CH₂ | HCl | 48 | 197-9 dec | 56.00 | 9.76 | 10.05 | (Cl 12.72) | 55.99 | 9.68 | 10.05 | (Cl 12.96) | II |
| HOCH₂CHOHCH₂ | | 73 | 70-3 | 55.36 | 9.29 | 10.76 | | 55.68 | 9.20 | 10.59 | | II |
|  | | 70 | 65-7 | 63.68 | 9.80 | 12.38 | | 63.82 | 9.82 | 12.60 | | Ic |
| CF₃C(=O) | | 75 | 66-8 | 46.81 | 6.07 | 9.92 | | 46.76 | 6.40 | 10.12 | | III |
| CH₃CCH₂ (=O) | HCl | 66 | 164-6 dec | 51.70 | 8.32 | 10.05 | (Cl 12.72) | 51.66 | 8.17 | 9.96 | (Cl 12.89) | II |
| CH₃CHOHCH₂ | HCl | 39 | 194-9 dec | 51.33 | 8.97 | 9.98 | (Cl 12.63) | 51.45 | 8.91 | 10.02 | (Cl 12.87) | II |
| HOCH₂CH₂OCH₂CH₂ | HCl | 81 | 145-6 | 50.23 | 8.76 | 9.01 | (Cl 11.41) | 50.04 | 8.52 | 8.90 | (Cl 11.56) | II |
| CH₃CCH₂CH₂ (=O) | | 55 | 63-5 | 60.91 | 9.44 | 10.93 | | 61.06 | 9.67 | 10.82 | | IV |
| NCCH₂CH₂CH₂ | HCl | 34 | 185-7 dec | 53.88 | 8.35 | 14.50 | (Cl 12.23) | 53.87 | 8.32 | 14.34 | (Cl 12.16) | II |
| H₂NCCH₂CH₂ (=O) | | 78 | 96-8 | 56.01 | 9.01 | 16.33 | | 56.05 | 9.04 | 16.50 | | IV |
| C₆H₅CH₂O | | 62 | 59-61 | 65.73 | 8.27 | 9.58 | | 65.47 | 8.20 | 9.57 | | VIII |
| p-(C₆H₅CH₂O)C₆H₄CH₂ | maleate | 44 | 180-2 dec | 65.04 | 6.87 | 5.62 | | 64.91 | 6.92 | 5.45 | | II |
| NCCH₂CH₂ | | 79 | 51-3 | 60.23 | 8.84 | 17.56 | | 60.19 | 8.43 | 17.75 | | II |
| p-HOC₆H₄CH₂ | maleate | 33 | 176-8 dec | 58.81 | 6.91 | 6.86 | | 58.99 | 6.84 | 6.82 | | IX |
| CH₃O | | 16 | 55-65(0.15) | 55.53 | 9.32 | 12.95 | | 55.61 | 9.13 | 12.96 | | X |
| p-CH₃COC₆H₄CH₂ (=O) | maleate | 12 | 174-6 dec | 58.66 | 6.71 | 6.22 | | 58.86 | 6.75 | 6.12 | | II |
| CH₃CH₂NCCH₂ (=O, H) | | 42 | 67-9 | 57.54 | 9.29 | 15.48 | | 57.46 | 9.11 | 15.56 | | II |
| CH₃CH₂SO₂CH₂CH₂ | | 88 | 80-2 | 50.96 | 8.55 | 9.14 | (S 10.46) | 50.90 | 8.48 | 8.96 | (S 10.48) | IV |
| H₂NC(=O) CHCH₂ (CH₃) | | 84 | 126.5-8 | 57.54 | 9.29 | 15.49 | | 57.52 | 9.32 | 15.55 | | IV |

Table 1-continued
| R | Acid Salt | Yield (%) | M.P. or B.P. (mm) °C. | Calculated (%) C | H | N | (Other) | Found (%) C | H | N | (Other) | Method Used |
|---|---|---|---|---|---|---|---|---|---|---|---|---|
| CH₃CH₂CH₂ | HCl | 29 | 200-2 dec | 54.43 | 9.52 | 10.58 | (Cl 13.39) | 54.23 | 9.44 | 10.54 | (Cl 13.47) | II |
| 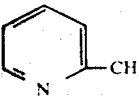 | maleate | 83 | 135°-6° | 58.00 | 6.92 | 10.68 | | 57.85 | 7.07 | 10.68 | | II |
| C₆H₅OCO₂CH₂CH₂ | HCl | 25 | 203.5°-4° | 56.02 | 6.79 | 7.26 | (Cl 9.19) | 56.25 | 6.59 | 7.08 | (Cl 9.12) | XI |
| H₂NCOCH₂CH₂ | | 81 | 136°-6.5° | 52.73 | 8.48 | 15.37 | | 52.87 | 8.25 | 15.46 | | XII |
| 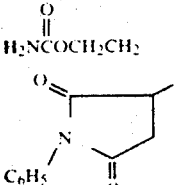 | | 50 | 152°-4° | 63.49 | 7.01 | 11.69 | | 63.88 | 7.21 | 11.82 | | IV |
| 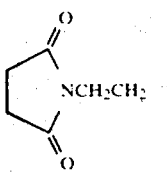 | HCl | 37 | 203°-5°dec | 51.80 | 7.53 | 12.08 | (Cl— 10.19) | 51.93 | 7.36 | 12.19 | (Cl— 10.09) | II |
| 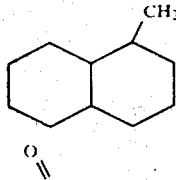 | Maleate | 62 | 145°-7°dec | 62.01 | 7.01 | 9.43 | | 62.10 | 7.09 | 9.29 | | XIII |
| 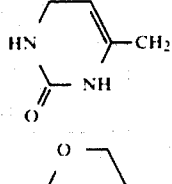 | | 60 | 232°-3° | 54.18 | 7.15 | 18.05 | | 54.09 | 7.18 | 17.84 | | II |
| 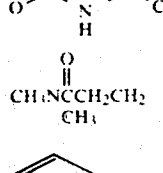 | | 10 | 153.5°-5.5° | 54.72 | 8.12 | 14.73 | | 54.84 | 8.08 | 14.82 | | II |
| CH₃NCCH₂CH₂ CH₃ | Maleate | 55 | 161°-2° | 53.85 | 7.78 | 10.47 | | 53.85 | 7.64 | 10.26 | | IV |
| 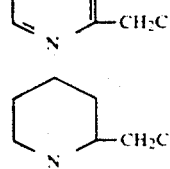 | Maleate H₂O | 13 | 135.5-7 | 56.46 | 7.34 | 9.86 | | 56.63 | 6.94 | 9.50 | | II |
| 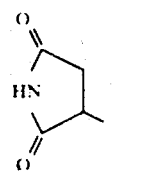 | 2 Maleate | 84 | 184-5.5 | 54.43 | 7.42 | 7.93 | | 54.21 | 7.32 | 7.95 | | XIV |
|  | | 90 | 177.5-8.5 | 55.11 | 7.47 | 14.83 | | 55.03 | 7.57 | 14.84 | | IV |

Table 1-continued

| R | Acid Salt | Yield (%) | M.P. or B.P. (mm) °C. | Calculated (%) C | H | N | (Other) | Found (%) C | H | N | (Other) | Method Used |
|---|---|---|---|---|---|---|---|---|---|---|---|---|
| 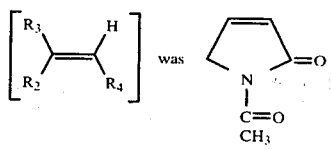 | | 55 | 115–5.5 | 63.68 | 9.80 | 12.38 | | 64.59 | 9.78 | 12.57 | | II |
| $CH_3SCH_2CH_2$ ↓ O (sulfoxide) | oxalate | 31 | 177–8 | 45.88 | 7.15 | 7.65 | | 45.61 | 7.24 | 7.39 | | II |
| $H_2NC(=O)CH_2CH_2CH_2$ · ¼ $H_2O$ | | 7 | 67.5–71.5 | 56.60 | 9.32 | 15.23 | | 56.58 | 9.41 | 15.23 | | XIV |
| (4-methyl-2-pyrrolidinone, HN attached) | | 29 | 157–8.5 | 57.97 | 8.61 | 15.60 | | 57.76 | 8.73 | 15.51 | | IV[1] |
| (5-methyl-2-pyrrolidinone) | - | 6 | 170–3 | 57.97 | 8.61 | 15.60 | | 57.78 | 8.78 | 15.27 | | IV[1] |

[1] Both products obtained from the same reaction. Starting material $$\begin{bmatrix} R_3 & H \\ R_2 & R_4 \end{bmatrix} \text{ was } \underset{\underset{CH_3}{C=O}}{\underset{|}{N}}\!\!\!\!\!\!\!\!\!\!\!\!\!\!\!\text{(1-acetyl-3-pyrrolin-2-one)}=O$$

Other compounds of Formula (I) where $R_1$ is C≡CH and R has a value as indicated are shown in Table II below.

Table III summarizes the preparation of other piperazines according to the invention where $R_1$ is —CH=CH$_2$ and R has a value as shown.

Table II

| R | Acid Salt | Yield (%) | M.P. or B.P.(mm) °C. | Calculated (%) C | H | N | (Other) | Found (%) C | H | N | (Other) | Method Used |
|---|---|---|---|---|---|---|---|---|---|---|---|---|
| $CH_3$ | HCl | 28 | 212–4 dec | 53.35 | 7.76 | 11.35 | (Cl 14.37) | 53.67 | 7.88 | 11.41 | (Cl 14.60) | Ia |
| $C_6H_5CH_2$ | HCl | 29 | 213–5 dec | 63.25 | 7.18 | 8.68 | (Cl 10.98) | 63.57 | 7.39 | 8.45 | (Cl 11.11) | Ia |
| H | HCl | 72 | 193–4 dec | 51.61 | 7.36 | 12.04 | (Cl 15.23) | 51.37 | 7.39 | 11.92 | (Cl 15.19) | Id |
| $H_2NC(=O)CH_2$ | | 76 | 152.5–5 dec | 56.90 | 7.56 | 16.59 | | 56.98 | 7.62 | 16.65 | | II |
| $CH_3CH_2CH_2$ | HCl | 35 | 191–3 dec | 56.83 | 8.44 | 10.19 | (Cl 12.90) | 56.46 | 8.20 | 10.01 | (Cl 13.01) | II |
| $H_2NC(=O)CH_2CH_2$ | | 91 | 92–4 | 58.41 | 7.92 | 15.72 | | 58.45 | 7.78 | 15.66 | | IV |
| $CH_3C(=O)CH_2$ | HCl | 63 | 188–90 dec | 54.07 | 7.33 | 9.70 | (Cl 12.28) | 54.16 | 7.32 | 9.58 | (Cl 12.53) | II |

Table III

| R | Acid Salt | Yield (%) | M.P. or B.P.(mm) °C | Calculated (%) C | H | N | (Other) | Found (%) C | H | N | (Other) | Method Used |
|---|---|---|---|---|---|---|---|---|---|---|---|---|
| CH₃ | maleate | 37 | 132–4 dec | 54.87 | 7.37 | 8.53 | | 54.83 | 7.42 | 8.46 | | Id |
| C₆H₅CH₂ | maleate | 18 | 145–7 dec | 62.36 | 6.98 | 6.93 | | 62.34 | 7.25 | 6.75 | | Id |
| H₂NC CH₂CH₂ ‖ O | | 20 | 70–3.5 | 57.97 | 8.61 | 15.60 | | 57.70 | 8.39 | 15.81 | | IV |

As noted, the piperazines of formula (I) demonstrate analgesic and antidepressant activity. Most of the exemplified compounds show both antidepressant and analgesic activities although in some instances, one or the other activity may be stronger. In general, the antidepressant activity of the compounds of formula (I) as measured in standard experimental tests compares favorably with that of Imipramine which, as noted, is a well known compound for the treatment of depressed states. The tests employed involve determination of the activity of the compounds as antagonists of tetrabenazine ptosis induced in mice and of muricidal behavior in rats, as compared to the activity of Imipramine. In the first of these tests, mice (approximately 18–25 grams) were treated with tetrabenazine which induces ptosis (eyelid closure). Oral dosages of the test compounds were then administered to determine the capacity of the drug to prevent tetrabenazine-induced ptosis. The capacity of the drug candidate as an antagonist for tetrabenazine was measured by % protection of ptosis and is indicative of the degree of antidepressant activity.

Some rats will spontaneously attack and kill mice (muricidal behavior) and this behavior can be selectively (i.e. at doses that do not produce ataxia) antagonized by clinically effective antidepressants (e.g. Imipramine). Male Long-Evans hooded rats were used for these studies; following intraperitoneal administration of the drug, the rats are tested for killing behavior at 30 and 60 minutes post-drug administration and are tested for neurological impairment (ataxia) on a 45° inclined screen immediately thereafter. Thus, potency as an antagonist of muricidal behavior is used as a predictor of clinical antidepressant activity.

The analgesic activity of the piperazines contemplated for use herein also compares favorably with the analgesic activity of reference standards, such as aspirin and Meperidine hydrochloride, as determined by standard animal tests. The analgesic activity is demonstrated on the Carrageenan Inflamed Paw Pressure Test and the Mouse Writhing Test. In the former, adult male albino Wistar rats weighing approximately 160–180 grams are fasted. The test compound is then administered orally prior to injection of the phlogistic agent (carrageenan). All drugs are suspended in an HPMC vehicle. A preparation of sodium carrageenan, as a 1% suspension in sterile 0.9% sodium chloride is injected (0.1 ml) intradermally into the plantar tissue of the right hind paw. Analgesic activity is measured 45 minutes post-drug administration by measuring the latency to respond (vocalization and/or biting) to linearly increasing pressure on the inflamed paw. Any treated rat exhibiting a reaction time equal to or greater than the placebo group's mean reaction time plus two standard deviations is considered to be significantly affected.

The Mouse Writhing Test is another standard for determining analgesic activity (Collier et al., Brit. J. Pharmac. Chemother., 1968, 32, 295; Whittle, Brit. J. Pharmac. Chemother., 1964, 22, 246). This test is carried out as follows:

A painful stimulus is produced by injection of a 0.6% aqueous solution of acetic acid or 6.0 mg/kg. of acetylcholine bromide into the peritoneal cavity of a male mouse (18–22 grams). The characteristic response to this painful stimulus is an abdominal constriction in conjunction with a stretching of the body.

In the acetylcholine writhing test, male albino Swiss-Webster mice (18–22 grams) are challenged with acetylcholine bromide (6.0 mg/kg, i.p.) 45 minutes after oral administration of test drug or placebo in a volume of 10 ml/kg. A writhe is defined as a pattern of movements usually consisting of arching of the back, pelvic rotation, and hind limb extension. Total number of writhes are counted for each mouse for a 3-minute period beginning immediately after acetylcholine administration. Any drug-treated mouse that exhibits a total number of writhes during the 3-minute test session equal to or less than one-half of the mean total of writhes for the same day control group is considered to be significantly inhibited. The ED50, that dose of drug that would be expected to significantly inhibit writhing in 50% of the mice tested, is also calculated.

In the acetic acid writhing test, groups of six male Swiss-Webster mice (18–22 grams) are injected intraperitoneally with 10 ml/kg of 0.6% aqueous acetic acid 30 minutes after oral administration of test drug. The mice are then placed in a plexiglass chamber for observation, and the number of writhes for each animal are counted during a 10-minute period starting 3 minutes after acetic acid treatment. Any drug-treated mouse that exhibited a total number of writhes during the 10-minute test session equal to or less than one-half of the mean total of writhes for the same day placebo-treated control group is considered to be significantly affected. The ED50, that dose of test drug that would be expected to significantly antagonize writhing in 50% of the mice tested, is also calculated.

Using the paw pressure test, the preferred compound of the invention (i.e. Compound A wherein R is aminocarbonylethyl and R₁ is CH₃ in formula I) increased the pain threshold by 57% at a dosage of 100 mg/kg body weight. On the mouse writhing test (acetic acid), Compound A gave a value of 100 (percent protection against challenge) at a dose of 100 mg/kg. These results compare favorably with reference standards. Thus, for example, Compound A demonstrates an activity about two times that of aspirin and about equal to that of meperidine on the acetic acid writhing test.

The ED$_{50}$ for Compound A on the acetic acid writhing test is about 20.5 (mg/kg, p.o.). This compares with an average value of 18.8 for meperidine and 56.0 for aspirin.

In general the esters of the invention demonstrate analgesic activity in mice in laboratory tests when administered orally at a dose of about 5 mg to 100 mg/kg body weight.

When tested for antidepressant activity against induced tetrabenazine ptosis, Compound A gave 100% protection at a dose of 30 mg/kg. The $ED_{50}$ for the compound was determined to be 10.2. On the induced muricide syndrome test, Compound A gave 60% protection at 30 minutes and at 60 minutes at a dose (i.p.) of 10 mg/kg with an $ED_{50}=4.9$. Here again, the results compared favorably with reference standards.

Based on the activities the present piperazine derivatives demonstrate in the animal standard tests and a comparison of these with the activities of presently used antidepressants and analgesics on these same tests, it is anticipated that pharmaceutical compositions of the invention may, in general, be administered to man for the treatment or prevention of depression and pain at an oral dose of between about 20 mg. and 300 mg. of active ingredient, an intramuscular or subcutaneous dose of between 20 and 150 mg. of active ingredient or an intravenous dose of between 15 and 75 mg. of active ingredient, the composition being administered 2 or 4 times per day. It will, however, be appreciated that the amount of piperazine derivative administered will vary depending on the compound used and the degree of pain or depression to be dealt with. The analgesic and antidepressant activity of the piperzine derivatives may be readily compared with conventionally available antidepressants, e.g. Imipramine, and analgesics, e.g. meperidine, to determine the best amount to use for any particular situation. It is noted, for example, that the preferred compound (Compound A) shows an antidepressant activity which is about the same as that of Impramine on the tetrabenazine ptosis reversal (TBZ) test. Impramine is used at a dosage of about 100 mg per day (25 mg, 4 times daily) in humans of average size. Accordingly, it is expected that Compound A would be used for antidepressant effect in humans at essentially the same dosage as Impramine.

The following examples are given to illustrate representative pharmaceutical compositions which are contemplated for use herein. While specific carriers and excipients are referred to in these examples, it will be appreciated that any of the well-known pharmaceutical carriers or additives can be used to prepare compositions according to the invention in acceptable dosage forms so as to provide an effective amount or a therapeutically effective amount of the active piperazine ester to be administered.

EXAMPLE A

This example illustrates the preparation of a tablet containing 100 mg. of Compound A:

| Formulation | Amounts (grams) |
| --- | --- |
| Compound A | 100 |
| Starch | 80 |
| Powered Lactose | 80 |
| Talc | 20 |
| Total Weight of Mix | 280 |

The above ingredients are combined, mixed and then compressed into slugs. The slugs may then be ground to form granules that will pass through a 14 to 16 mesh screen. The granules may then be recompressed into tablets using a suitable compression mold to form tablets, each weighing 280 mg.

EXAMPLE B

Capsules containing 200 mg. of Compound A or other active piperazine derivative according to the invention may be prepared by uniformly mixing together the active compound and powdered lactose in a ratio of 200 mg. active to 100 mg. lactose. The resulting powder mix may then be packed into an appropriately sized gelatin capsule (No. 1).

EXAMPLE C

An injectable composition suitable for intramuscular, intraperitoneal or subcutaneous injection may be prepared by mixing together 5.0 grams of a suitably soluble active compound, e.g. the hydrochloride salt of a compound according to Formula I wherein R and $R_1$ are both $CH_3$ with the following:

| | |
| --- | --- |
| Chlorobutanol | 3.0 grams |
| Propylene Glycol | 20.0 ml |
| Water for Injection q.s. | 1000.0 ml |

The resulting mixture is clarified by filtration and may then be placed into vials (containing 5 mg. active) which are sealed and autoclaved.

It will be appreciated that various modifications may be made in the invention is defined in the following claims wherein:

What is claimed is:

1. A method for obtaining an anti-depressant or analgesic effect in a host in need of such effect which comprises administering to said host an effective antidepressant or analgesic amount of a compound of formula (I)

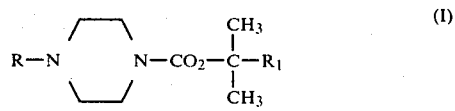

wherein R is an aminocarbonylalkyl wherein the alkyl contains 1 to 4 carbon atoms, and $R_1$ is $-CH_3$, $-CH=CH_2$ or $-C\equiv CH$, or a pharmaceutically acceptable acid-addition salt thereof.

2. The method of claim 1 wherein R is aminocarbonylethyl and $R_1$ is $CH_3$.

3. The method of claim 1, wherein R is aminocarbonylmethyl.

4. The method of claim 1, wherein R is aminocarbonylethyl.

5. The method of claim 1, wherein R is $H_2NCOCH(CH_3)CH_2-$.

6. The method of claim 1, wherein $R_1$ is $-CH_3$.

7. The method of claim 1, wherein said pharmaceutically-acceptable salt is selected from the group consisting of a hydrochloride, hydrobromide, phosphate, sulphate, citrate, acetate, maleate and oxalate.

8. A pharmaceutical composition for the treatment of depression or pain comprising an effective anti-depressant or analgesic amount of a compound of the formula

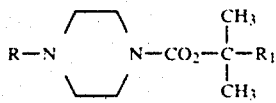

wherein R is an aminocarbonylalkyl wherein the alkyl contains 1 to 4 carbon atoms, and $R_1$ is $-CH_3$, $-CH=CH_2$ or $-C\equiv CH$, or a pharmaceutically acceptable acid-addition salt thereof, and a pharmaceutically acceptable carrier therefor.

9. A composition according to claim 8 wherein the compound is one wherein R is aminocarbonylethyl and $R_1$ is $CH_3$.

10. The composition according to claim 8 wherein the compound is one wherein R is aminocarbonylmethyl.

11. The composition according to claim 8 wherein the compound is one wherein R is aminocarbonylethyl.

12. The composition according to claim 8 wherein the compound is one wherein R is $H_2NCOCH(CH_3)CH_2-$.

13. The composition according to claim 8 wherein the compound is one wherein $R_1$ is $-CH_3$.

14. The composition according to claim 8 wherein said salt is selected from the group consisting of a hydrochloride, hydrobromide, phosphate, sulphate, citrate, acetate, maleate and oxalate.

15. An ester of a piperazine-1-carboxylic acid of the formula

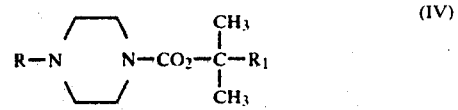

wherein R is an aminocarbonylalkyl wherein the alkyl contains 1 to 4 carbon atoms and $R_1$ is $-CH_3$, $-CH=CH_2$ or $-C\equiv CH$, or a pharmaceutically acceptable acid-addition salt thereof.

16. An ester according to claim 15 wherein R is aminocarbonylethyl and $R_1$ is $CH_3$.

17. The ester according to claim 15 wherein R is aminocarbonylmethyl.

18. The ester according to claim 15 wherein R is aminocarbonylethyl.

19. The ester according to claim 15 wherein R is $H_2NCOCH(CH_3)CH_2-$.

20. The ester according to claim 15 wherein $R_1$ is $-CH_3$.

21. The ester according to claim 15 wherein the salt is selected from the group consisting of a hydrochloride, hydrobromide, phosphate, sulphate, citrate, acetate, maleate and oxalate.

* * * * *